United States Patent [19]

Emde

[11] Patent Number: 4,692,152

[45] Date of Patent: Sep. 8, 1987

[54] MEDICAL TUBE

[75] Inventor: Carsten Emde, Berlin, Fed. Rep. of Germany

[73] Assignee: Fresnius AG, Fed. Rep. of Germany

[21] Appl. No.: 712,265

[22] Filed: Mar. 15, 1985

[30] Foreign Application Priority Data

Mar. 16, 1984 [DE] Fed. Rep. of Germany ....... 3409663

[51] Int. Cl.[4] ............................................ A61M 5/00

[52] U.S. Cl. .................................... 604/164; 604/270; 604/265

[58] Field of Search ............... 604/164, 166, 170, 270, 604/264, 265, 280, 282

[56] References Cited

U.S. PATENT DOCUMENTS

| | | | |
|---|---|---|---|
| 2,118,631 | 5/1938 | Wappler | 604/170 |
| 2,489,067 | 11/1949 | Wild | 604/270 |
| 2,508,690 | 5/1950 | Schmerl | 604/265 |
| 2,603,217 | 7/1952 | McShirley | 604/265 |
| 3,736,939 | 6/1973 | Taylor | 604/265 |
| 3,780,740 | 12/1973 | Rhea | 604/270 |
| 3,938,529 | 2/1976 | Gibbons | 604/282 |
| 4,257,421 | 3/1981 | Beal | 604/265 |
| 4,306,563 | 12/1981 | Iwatschenko | 604/265 |
| 4,390,017 | 6/1983 | Harrison et al. | 604/270 |
| 4,410,320 | 10/1983 | Dykstra et al. | 604/270 |
| 4,431,426 | 2/1984 | Groshong et al. | 604/164 |
| 4,490,143 | 12/1984 | Quinn et al. | 604/270 |
| 4,515,593 | 5/1985 | Norton | 604/265 |
| 4,516,970 | 5/1985 | Kaufman et al. | 604/270 |

FOREIGN PATENT DOCUMENTS

| | | | |
|---|---|---|---|
| 2546069 | 11/1984 | France | 604/264 |

*Primary Examiner*—Stephen C. Pellegrino
*Attorney, Agent, or Firm*—Omri M. Behr

[57] ABSTRACT

Medical probe or tube suitable in particular for enteral feeding and comprising a flexible tube which has at its distal end a closure cap and at its proximal end a connecting means, and a mandrin with securing means formed corresponding to the connecting means, wherein at the distal end of the tube near the closure cap in the tube openings are disposed and the closure cap has a gelatin coating, and preferably on the closure cap over the gelatin coating a further coating of gastric-juice-resistant material is disposed and preferably in the cap a metal head is located.

10 Claims, 3 Drawing Figures

MEDICAL TUBE

The present invention relates to a medical tube, in particular for enteral feeding, comprising a flexible tube which has at its distal end a loading body and in the region of its distal end at least one opening, at least a part of the loading body being removable after placing the tube.

Medical tubes for enteral feeding, i.e. by the intestinal route, are already known. Generally, these tubes consist of the actual flexible tube at the distal end of which a closure cap is disposed and the proximal end of which comprises connection means via which the tube is connected to the feeding pump and further supply means (such as further tubes and the like) for the food and the like or to the mandrin, as well as a mandrin or guide. The mandrin serves for temporary stiffening of the relatively soft feeding tube. It facilitates placement of the tube and after placement or insertion of the latter is removed. As material for the feeding tube generally PVC, polyurethane or silicone is used whilst the closure cap consists of polyethylene or silicone.

Tube feeding has become of increasing significance in recent years. An indication requiring artificial feeding is always the case when a patient must not eat, cannot eat, or does not want to eat. The particular nutritional therapy is adapted to the condition of the particular patient. This alimentary therapy is of significance not only in post-operative or post-traumatic areas but also in diseases which involve a disturbance in intake or digestion of nutrients and as supplementary therapy for cancer patients. Thus, tube feeding is carried out in the case of oral diseases, for example operations in the area of the mouth and maxillary sinuses, paralysis of the masticatory muscles, lengthy unconsciousness, for example cranio-cerebral traumas, patients on artificial respiration and relaxed patients, for example tetanus patients, patients refusing to take food for psychogenic reasons, e.g. anorexia, cancer patients who frequently have taste disturbances, and in pediatry. Investigations have shown that tube feeding, compared with total parenteral feeding, involves fewer and less serious complications and in addition is more economical than parenteral feeding. This means that tube feeding is more advantageous than parenteral feeding and with few exceptions is the prefered therapy for malnutrition.

In general, a distinction is made between nasogastric, nasoduodenal and nasojejunal tube feeding. For nasoduodenal and nasojejunal feeding hitherto tubes have been used having a closure cap as guide bolus (e.g. of mercury or water). Placement of the feeding tube requires however an intact gastroduodenal peristalsis.

On occasion, these tubes may also be placed during an operation. The nasoduodenal and nasojejunal feeding tubes are used above all in the field of conservative medicine for unconscious patients, patients on continuous artificial respiration, relaxed patients and premature babies. In addition they are of undisputed importance in surgery for patients with acute malnutrition in the preparation for operations, as alternative to an operation and in follow-up treatment (e.g. chemotherapy or radiotherapy of malignant tumours). Particularly when used for feeding unconscious patients, cancer patients, premature babies and small children, who cannot themselves actively assist during placement, insertion of the tubes when using existing types involves considerable difficulties and problems and consequently frequently the selective successful feeding of these patients is not satisfactorily ensured.

Tubes are already known which comprise as guide bolus a balloon which can be filled with a liquid, for example mercury or water, with the aim of facilitating placement of the flexible tube. Such tubes are known from DE-PS No. 3,105,883, DE-OS No. 2,914,609, DE-OS No. 2,402,573, DE-OS No. 2,524,030, DE-OS No. 2,810,326, DE-PS No. 2,721,540, the article by Rueff et al. in "Münchner Medizinische Wochenschrift (1968, page 470–474) and the catalog of the company Rüsch (1977, pages 15–19). In the first patent specification above the balloon is adhered to the tube with an agent soluble in the small intestine and can be removed by detachment after placement.

All known tubes having a balloon have the disadvantage that initially on placing through the nose they can only be filled to a limited extent, i.e. placing in the nose itself already involves difficulties.

On further movement of the tube through the esophagus the balloon is then filled with the liquid. Here as well considerable difficulties are encountered on continuation of the movement of the tube through the esophagus because the liquid contained in the balloon yields to the peristaltic movement of esophagus and stomach so that serious placement problems are also encountered here. On the other hand, hitherto only tubes have been used with a metallic closure cap at the distal end which was only slightly thicker than the tube itself so that this provided no assistance in placement.

The invention is thus based on the problem of further developing the tube of the type mentioned at the beginning in such a manner that it can be moved without any problem through the peristaltic movement of the esophageal and gastro-intestinal tract, is reliably located after placement and does not disturb the digestive process.

The solution of this problem resides in that the load body comprises a firm cap having a thickening layer of a material absorbable by the body of the patient.

A closure cap enlarged in this manner offers a better engagement point for the peristalsis of esophagus, stomach and/or intestine, which is particularly important with passive patients (e.g. unconscious or comatose patients).

Suitable materials absorbably by the body of the patient are pharmacologically harmless solidifying substances, such as agar, alginic acid, starches, gum arabic, pectin, PVP, methyl cellulose and gelatin, gelatin being preferred.

Suitable as gelatin are all commercially available gelatins which can be used for medical purposes, such as soft gelatins and hard gelatins, or gelatin compositions possibly containing other additives suitable for medical purposes such as softeners (for example sorbite), glycerol, alkali salts (sodium salts) of ethyl p-hydroxybenzoate or propyl p-hydroxybenzoate, and water or the like. Preferably, soft gelatins or a gelatin composition is used containing apart from gelatins also sorbite, glycerol, the sodium salt of ethyl p-hydroxybenzoate, the sodium salt of propyl p-hydroxybenzoate and water. A suitable and preferred composition of the gelatin composition according to the invention is as follows:

| | Content in % | |
|---|---|---|
| Constituents | preferred | in particular |
| Gelatin | 40–50 | 44.35 |

-continued

| Constituents | Content in % | |
|---|---|---|
| | preferred | in particular |
| Sorbite 60–70% aqueous solution | 5–15 | 10.3 |
| Glycerol | 45–15 | 10.2 |
| Ethyl p-hydroxybenzoate Na salt | 0.10–0.3 | 0.19 |
| Propyl p-hydroxybenzoate Na salt | 0.05–0.15 | 0.09 |
| Water | 30–40 | 34.85 |

These gelatins are digested after placement of the tube.

The thickness of the thickening layer is not critical but the coating layer should be so thick that the placement of the tube is improved to the desired extent but on the other hand the placement of the tube is not restricted, i.e. should be such that the tube bolus offers a favorable engagement point for the peristalsis. Suitable thicknesses are 3–6, in particular 4–5 mm with a tube diameter of about 2 mm. Of particular importance is the thickness jump between the thickening layer and the tube because this jump ensures improved tube transport. Advantageously, the thickness jump (or the maximum wall thickness of the thickening) is in a range of 0.5–2, preferably 1–1.5 mm.

The thickening layer can be applied directly to the distal end of the feeding tube or to a cap or plug disposed in the distal end of the tube and consisting of suitable physiologically compatible material such as hard gelatins or plastic (e.g. of polyolefin, in particular polyethylene or silicone).

Preferably, on the thickening layer of the closure cap a covering or further coating layer of acid-resistant material is disposed. This further covering layer not only further enlarges and strengthens the closure cap or tube tip and thus further facilitates placement of the feeding tube but in particular for nasoduodenal and/or nasojejunal feeding provides a tube which due to the enlargement of the closure cap or tube tip (bolus) even in passive patients easily passes through the stomach unattached by gastric acid and can be safely and reliably placed in the duodenum or jejunum. The material used for this further covering layer is one which is resistant to gastric acid, i.e. gastric juice, but is soluble in the intestinal juice, i.e. in the environment of the intestine. Examples of such materials are physiologically harmless materials such as anionic polymers of methacrylic acid and methyl methacrylate, and mixtures thereof with other materials and with each other. Preferred are anionic polymers of methacrylic acid and methyl methacrylate, such as Eudragit S, Eudragit L and mixtures thereof (made by Röhm Pharma), in particular Eudragit S. Also suitable as covering material is shellac and cellulose acetate phthalate as coating material.

The thickness of the coating layer is not critical but the covering layer should be thick enough to protect the thickening layer from the attack of the stomach juices but on the other hand not so thick that it dissolves too slowly, thus preventing possible removal of the tube from the duodenum or jejunum. Suitable thicknesses are about 10–30 μm, in particular about 25 μm. The coating can be colorless, transparent, white or pigmented in some color; preferably, it is adapted to the color of the feeding tube.

To further facilitate placing the tubes, in particular nasoduodenal and nasojejunal tubes, the closure cap can advantageously have a metal head or metal plug or stopper disposed at the distal end of the feeding tube. Such a metal head increases the weight of the tube and stiffens the distal end thereof and thus considerably facilitates insertion or placing of the tube, in particular in the case of passive patients.

Suitable materials for the metal head or metal plug are metals harmless in medical uses, such as special steel, noble metals and the like. In particular, metal heads or plugs of V4A and V2A steel are used.

The size of the metal head is not critical and should be in the usual size range for closure caps or can be somewhat smaller; it should however be large enough for the metal head to perform the desired function. Conveniently, the metal head has substantially the same outer diameter as the tube whilst its length depends on the weight and holding in the tube. Similarly, the metal head can have any suitable form. It is preferably inserted by means of a neck in stopper manner into the distal end of the tube.

The thickening layer, on which preferably the covering layer of gastric-juice-resistant material soluble in intestinal juice is applied, is then applied directly to the metal head or via a cap possibly surrounding said head and consisting of suitable physiologically safe material such as hard gelatins or plastic (e.g. polyolefin, such as polyethylene or silicone).

The feeding tube itself consists of conventional material suitable for tubes and probes such as PVC, silicone or polyurethane, preferably of silicone or polyurethane.

For temporary stiffening of the relatively soft feeding tube a mandrin formed in the usual manner is used. With the metal head present according to the invention at the distal end of the tube the mandrin preferably opens into a recess or bore of the metal head or the neck portion of said metal head to prevent bending of the feeding tube at the tip. Preferably a bore is provided in the neck portion of the metal head.

The feeding tube preferably comprises in usual manner in the region of the distal end openings permitting discharge of the nutrient. The number of openings is not critical. However, the number of such openings should be sufficient to permit satisfactory food discharge. Preferably there are two to four, in particular three openings. Also, in usual manner marking lines are preferably provided on the feeding tube which serve as a guide during insertion of said tube.

The diameter and length of the feeding tube depend on the respective purpose and are within the usual range. Typically, nasogastric tubes are 75 cm long and have an inner diameter of 2–4 mm; nasoduodenal or nasojejunal tubes have a length of preferably 1.25 m, an internal diameter of 1.2–1.6 mm and an external diameter of 2–2.4 mm.

At the proximal end of the flexible tube conventional connection means are provided which serve firstly to secure the mandrin and subsequently after placement of the tube in usual manner for receiving or connection of lines and tubing via which the tube is connected to the feeding pump and other supply lines for the feeding substance. These connection means may for example be in the form of a connector with Luer connection, a plug-type connection or the like. Preferably, a plug-type connection or a connector with Luer cone is used, in particular a connector with Luer cone.

The feeding tube according to the invention is made in the usual manner. According to the preferred embodiment using the metal head for example said head is preferably inserted into the distal end of the tube with a neck-shaped portion of the metal head in plug manner. Thereafter, for example, the distal end of the feeding tube equipped with the metal head is provided with the thickening layer by dipping the end of the distal tube provided with the metal head in a heated gelatin composition and then withdrawing it in order to optionally provide it with a further coating of gastric-juice-resistant material, which can be done in usual manner, possibly by spraying on. Immersion of the distal end in the heated gelatin composition is preferably done by inclined dipping, i.e. dipping at an angle of less than 90°.

The present invention will be explained hereinafter with reference to the drawings, wherein.

Figure 1:
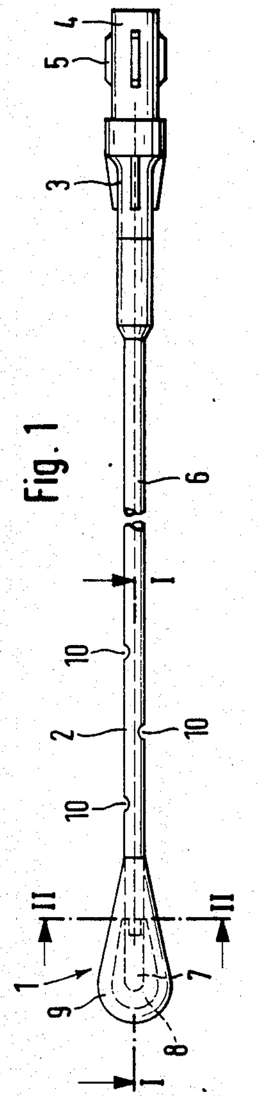
FIG. 1 is a schematic side view of a preferred embodiment of a feeding tube according to the invention.

In FIG. 1, 1 denotes the closure cap or tube tip or the bolus at the distal end of the tube according to the invention and 2 the flexible tube. At the proximal end of the feeding tube there is a usual connecting means 3 for the mandrin 6 or other supply or connecting lines which as illustrated can be in the form of a Luer connector or have any other form, for example in the form of a plug connector. Inserted in said connection means is the corresponding connection means 4 of the mandrin 6 preferably carrying the so called grip strips 5 to facilitate handling.

At the distal end of the feeding tube the metal head 7 is disposed in plug manner in the tube 2. On the metal head 7 is a thickening layer 8 of a material absorbable by the body of the patient, preferably gelatin, on which a covering layer 9 of a gastric-juice-resistant material soluble in intestinal juice (preferably Eudragit S) is preferably disposed. This thickening layer 8 preferably has the aforementioned dimensions.

In the region of the distal end in the tube one or more openings 10 are provided for the exit of the nutrient.

Figure 2:
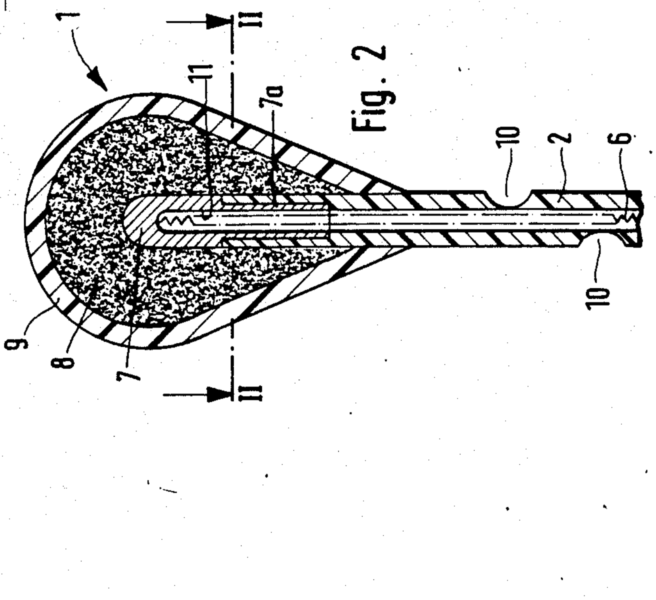
FIG. 2 is an enlarged longitudinal section through the distal end of the tube according to FIG. 1 along the line I—I.

FIG. 2 illustrates an enlarged longitudinal section through the region of the distal end and the closure cap or bolus of the tube according to the invention corresponding to FIG. 1, the reference numerals corresponding to those in FIG. 1. Clearly apparent in the enlarged illustration is the closure cap or tube tip or bolus 1 with the metal head which is fitted to the distal end of the tube 2 inserted with the neck portion *7a* in plug manner into the tube end. The neck portion *7a* of the metal head may possibly have a bore 11 for receiving the distal end of the mandrin 6. This metal head may also have another suitable form, for example may be pear shaped or substantially cylinder shaped.

As apparent from FIG. 2 there is first applied to the distal end of the tube 2 and the metal head 7 the thickening layer 8 and on the latter the covering layer 9 of gastric-juice-resistant material soluble in intestinal juice is applied. The openings 10 in the tube 2 serve for exit of the feeding substance.

Figure 3:
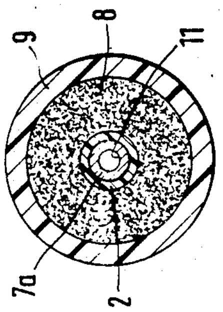
FIG. 3 is a cross-section through the distal end of the tube according to FIG. 1 or 2 along the line II—II.

The cross-section illustrated in FIG. 3 along the line II—II of FIG. 1 or 2 shows how the distal end of the feeding tube 2 surrounds the neck portion *7a* of the metal head 7 and is itself surrounded by the thickening layer 8 and the covering material 9 of a gastric-juice-resistant material soluble in intestinal juice.

I claim:

1. A medical device, particularly a catheter or feeding tube comprising: a tube having a passage therethrough, having a proximal end for receiving a flowable substance, a closed leading end portion closing the distal end of said tube, and at least one radial opening in said tube located close to but proximal from said closed end portion, said leading end portion comprising a metallic head portion having an axial bore journalled thereinto, and a withdrawable mandrin passing axially through said tube and into said bore in said head portion, and a substantially teardrop shaped bolus surrounding said metallic head portion, the portion of greater radius being at the distal end, said bolus comprising an inner segment of a pharmacologically harmless substance capable of being safely absorbed by the human system and a coating layer coating said inner segment of a physiologically acceptable material substantially resistant to stomach acids.

2. A device of claim 1 wherein the metal head is made of stainless steel.

3. A device of claim 1 wherein said leading end portion comprises:

a head portion and a neck portion of greater diameter, said neck portion being sized to fit snugly into the distal end of said tube.

4. A device of claim 1 wherein the absorbable material comprises gelatine.

5. A device of claim 1 wherein the resistant material comprises an anionic polymeric material selected from the group consisting of polymers of methacrylic acid, methyl methacrylate, copolymers thereof and mixtures of said polymers.

6. A medical device, particularly a catheter or feeding tube comprising:

a tube having a passage therethrough, having a proximal end for receiving a flowable substance, a closed leading end portion closing the distal end of said tube, and at least one radial opening in said tube located close to but proximal from said closed end portion, said leading end portion comprising a metallic head portion, a substantailly teardrop shaped bolus surrounding said metallic head portion, the portion of greater radius being at the distal end, said bolus comprising an inner segment of a pharmacologically harmless substance capable of being safely absorbed by the human system and a coating layer coating said inner segment of a physiologically acceptable material substantially resistant to stomach acids.

7. A device of claim 6 wherein the metal head is made of stainless steel.

8. A device of claim 6 wherein said leading end portion comprises:

a head portion and a neck portion of greater diameter, said neck portion being sized to fit snugly into the distal end of said tube.

9. A device of claim 6 wherein the absorbable material comprises gelatine.

10. A device of claim 6 wherein the resistant material comprises an anionic polymeric material selected from the group consisting of polymers of methacrylic acid, methyl methacrylate, copolymers thereof and mixtures of said polymers.

* * * * *